United States Patent [19]

McGuire

[11] Patent Number: 5,681,320

[45] Date of Patent: Oct. 28, 1997

[54] BONE-CUTTING GUIDE

[76] Inventor: David A. McGuire, 3418 Lakeside Dr., Anchorage, Ak. 99515

[21] Appl. No.: 622,615

[22] Filed: Mar. 26, 1996

Related U.S. Application Data

[63] Continuation of Ser. No. 347,578, Nov. 30, 1994, abandoned, which is a continuation-in-part of Ser. No. 180,956, Jan. 13, 1994, Pat. No. 5,562,669, which is a continuation-in-part of Ser. No. 956,733, Oct. 2, 1992, Pat. No. 5,391,170, which is a continuation-in-part of Ser. No. 806,906, Dec. 13, 1991, Pat. No. 5,257,996, which is a continuation-in-part of Ser. No. 839,466, Feb. 19, 1992, Pat. No. 5,520,693.

[51] Int. Cl.$^6$ ............................................. A61B 17/17
[52] U.S. Cl. .................. 606/104; 606/96; 606/98; 606/86; 606/88
[58] Field of Search ................. 606/104, 72, 73, 606/86, 87, 88, 96, 97, 98, 79, 80, 74

[56] References Cited

U.S. PATENT DOCUMENTS

| | | | |
|---|---|---|---|
| 2,200,120 | 5/1940 | Nauth | 606/97 |
| 3,867,932 | 2/1975 | Huene | 606/96 |
| 4,708,139 | 11/1987 | Dunbar, IV | 128/305 |
| 4,946,462 | 8/1990 | Watanabe | 606/148 |
| 5,078,719 | 1/1992 | Schreiber | 606/96 |
| 5,139,520 | 8/1992 | Rosenberg | 623/13 |
| 5,163,940 | 11/1992 | Bourque | 606/96 |
| 5,234,430 | 8/1993 | Huebner | 606/60 |
| 5,257,996 | 11/1993 | McGuire | 606/104 |

FOREIGN PATENT DOCUMENTS

| | | |
|---|---|---|
| 0 265 659 | 5/1988 | European Pat. Off. . |
| 2 679 126 | 1/1993 | France . |
| 85 94 736 | 10/1985 | Germany . |
| WO 93/09730 | 5/1993 | WIPO . |

*Primary Examiner*—Robert A. Hafer
*Assistant Examiner*—Benjamin Koo
*Attorney, Agent, or Firm*—Bromberg & Sunstein LLP

[57] ABSTRACT

A bone-cutting guide having a base with a cylindrical tunnel for guiding a cutting instrument therethrough. The guide is anchored to the bone in at least three locations. A positioning arm having a distal end anchors the guide within a joint. An anchoring pin is insertable through the base alongside the cylindrical tunnel to stabilize the guide against the bone being drilled. An embodiment of the invention includes two anchoring pins on either side of the cylindrical tunnel through the base. The positioning arm can be stabilized within a joint due to stabilizing spikes extending from the distal end of the arm. A curve is provided in the positioning arm between two spikes to provide an opening through which a reamer guided through the cylindrical tunnel maybe operated.

48 Claims, 4 Drawing Sheets

BONE-CUTTING GUIDE

This application is a continuation of U.S. application Ser. No. 08/347,578, filed Nov. 30, 1994 (now abandoned), which is a continuation-in-part of U.S. application Ser. No. 08/180,956, filed on Jan. 13, 1994 (now issued as U.S. Pat. No. 5,562,669), which is a continuation-in-part of U.S. application Ser. No. 07/956,733, filed on Oct. 2, 1992 (now issued as U.S. Pat. No. 5,391,170), which is a continuation-in-part of U.S. application Ser. No. 07/806,906, filed on Dec. 13, 1991 (now issued as U.S. Pat. No. 5,257,996), and Ser. No. 07/839,466 filed on Feb. 19, 1992 (now issued as U.S. Pat. No. 5,520,693).

BACKGROUND OF THE INVENTION

The present invention relates to the field of arthroscopic surgery, particularly anterior cruciate ligament reconstruction.

One common approach to cruciate ligament reconstruction is the use of the patellar tendon to form a bone-tendon-bone graft. This involves cutting out a bone block from the top of the patella. Deviations from proper technique for removal of the patellar bone block have resulted in reports of patellar tendinitis, patellar fractures and even, in some instances, ruptures of the patellar ligament after the grafting procedure. Whether or not these complaints are properly related to the use of the patellar bone block in cruciate ligament reconstruction, these concerns are reason enough to identify an alternate method for performing the surgery.

Cruciate ligament reconstruction involves the drilling of a tunnel through the tibia and into the femur. The tunnels are used for insertion of a graft to replace the damaged cruciate ligament. The accuracy in drilling these tunnels is critical to providing a satisfactory repair. A commonly used method of directing a drill to form these tunnels is by using a guide wire drilled through the bone first. The location of the guide wire can be tested before drilling out the tunnel. A cannulated drill is then inserted over the guide wire to drill the full size tunnel. When it has been desirable to retain the core of the bone tunnel being drilled, a coring reamer is used. However, when a coring reamer is used over a guide wire, the guide wire produces a stress riser in the bone core. Moreover, the use of a guide wire is generally inadequate to accurately guide a coring reamer throughout the drilling of an entire bone tunnel.

SUMMARY OF THE INVENTION

The present invention is directed, among other things, to a bone-cutting guide and related method for drilling bone to form, in one embodiment, a tibial tunnel and, if desired, a femoral tunnel. The construction of the guide may be replicated within the scope of the invention for use in other areas of the body for accurate use of a coring reamer. The tibial guide includes a base that has a cylindrical tunnel for guiding a cutting instrument such as a coring reamer therethrough. A positioning arm extends from the base and has a distal end anchoring against the tibia within a knee joint. At least one anchoring pin is insertable through the base alongside the cylindrical tunnel and into the tibia for rigidly stabilizing the guide. A coring reamer can be accurately guided by insertion through the cylindrical tunnel.

In accordance with an embodiment of the invention, the positioning arm can be adjustably mounted to the base within a range of angles. The preferred range is from about 50° to about 80° between a seating portion of the positioning arm and an axis through the cylindrical tunnel. In addition, a distal end of the positioning arm is provided with one or more spikes for stabilizing the end of the arm within the knee joint. The embodiment provides that the positioning arm is curved between a first spike and a second spike so that a cutting instrument such as a reamer operating through the cylindrical tunnel is directed through an opening created by the curve in the positioning arm.

The present invention in various embodiments is directed to a bone-tendon-bone composite graft for use in cruciate ligament reconstruction along with a tibial drill guide for forming the tibial tunnel, a trefoil rasp for forming channels in the bone tunnels and a bone block drill guide for forming the bone plugs of the graft. The method of the present invention is directed to ligament reconstruction surgery. In a preferred embodiment, a bone tunnel is formed in each of two bones of the joint. In knee surgery, these are the femur and the tibia. Preferably, the bone tunnel is formed by drilling a core out through the bone such that the core might be used to form the bone plug in the composite graft. The bone plugs are machined to form two longitudinal substantially parallel grooves opposite one another. At least one ligament replacement, such as a semitendinosus tendon, and/or gracilis, is extended between both of two bone plugs along the parallel grooves in each plug. The ligament replacement is attached to the two bone plugs. Each bone plug is inserted into one of the bone tunnels and secured therein by an interference screw. The use of the bone-tendon-bone composite graft of the invention results in a reconstructed cruciate ligament, also, in accordance with an embodiment the present invention.

The invention further includes in another embodiment a bone block drill guide for forming the bone plugs required in the composite graft of the present invention. The bone block drill guide includes a main hole for accommodating the bone plug. First and second parallel holes that intersect opposite sides of the main hole are used for directing a drill bit to cut a groove longitudinally along the bone block.

A trefoil rasp in accordance with an embodiment of the present invention is used to file channels in the bone tunnels. Two channels, oppositely located from one another, accommodate the ligament replacement attached between the two bone grafts. The third channel is generally located parallel to and equidistant from the other two channels. This third channel is used to guide an interference screw along the bone tunnel adjacent to the bone portion of the graft.

The composite graft in accordance with an embodiment of the present invention is advantageously formed without cutting into the patella. The trefoil rasp provides for interference screw fixation without permitting the screw to cut into the ligament replacement.

Other features of the present invention will become apparent during the following description taken in conjunction with the drawings.

BRIEF DESCRIPTION OF THE DRAWINGS

FIG. 3a is an isometric view of a trefoil rasp.

FIG. 3b is an end view of the rasp of FIG. 3a.

FIG. 4b is a side view of the bone plug of FIG. 4a.

3

FIG. 7b is a plan view of the bone block drill guide of FIG. 7a.

DETAILED DESCRIPTION OF PREFERRED EMBODIMENTS

Figure 1:
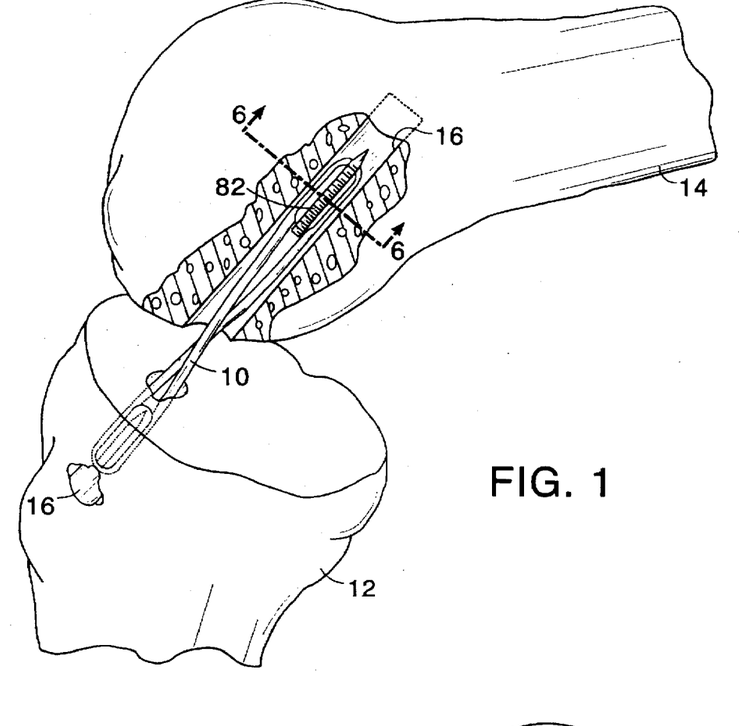
FIG. 1 is a perspective view in partial cross section of a reconstructed ligament formed with the present invention.

Referring now to the drawings, a reconstructed ligament for a knee joint is shown in FIG. 1 in accordance with an embodiment of the present invention. The cruciate ligament reconstruction surgical operation can be conducted as an open surgery, or preferably, through arthroscopic surgery. The arthroscopic surgical method presently preferred for carrying out the present invention shall now be described.

Arthroscopic diagnostic procedures are first conducted without tourniquet control in order to allow sufficient time for the ACL reconstruction procedure. Conventional anteromedial and distal lateral portals are drilled to give access to the knee joint for these procedures. The procedures may include meniscotomy, meniscal repair, removal of loose bodies, debridement of anterior cruciate ligament tear, etc. Notchplasty may be commenced under tourniquet control. The boundary of the notchplasty should be sufficiently wide (about 2 cm.) and sufficiently posterior to include the posterior lateral femoral cortex in order to ensure accurate placement and subsequent isometry.

In order to proceed with anterior cruciate ligament reconstruction, a vertical incision is made medial to the tibial tubercle approximately 2.5 cm. in length. The skin incision may be undermined in such a fashion as to provide sufficient mobility for retraction, while harvesting the tibial and femoral bone cores. A carefully placed anteromedial tibial incision may begin approximately 1 cm. medial to the tibial tubercle and 2 cm. distal to the joint line. Conventional surgical procedures are used to excise a semitendinosus tendon, and, if desired, the accompanying gracilis. While the use of the semitendinosus tendon and gracilis is one embodiment of the invention, alternative ligament replacement materials may be substituted for use in the composite graft of the invention.

The two major bones that meet at the knee joint are the tibia 12 and the femur 14. A bone tunnel 16 is drilled through each of these two bones. The tunnels 16 may be drilled with a regular drill that crushes and removes the bone within the tunnel. However, it is preferable to use a coring reamer to drill the bone tunnels. The reamer drills out a core of bone through each of the bone tunnels. The bone core can then be used to form a bone plug in the composite graft that will be replaced when reconstructing the ligament. In using the coring reamer to drill out a core that may be reused in the composite graft, it is important that a guide pin not be inserted into the core for directing the reamer. The hole formed by the guide pin through the center of the core would form a stress riser in the bone plug making the bone plug subject to fracture. A tibial guide 30 in accordance with an embodiment of the present invention properly orients and guides a coring reamer for making the bone tunnels without a guide wire.

4

Figures 2, 9:
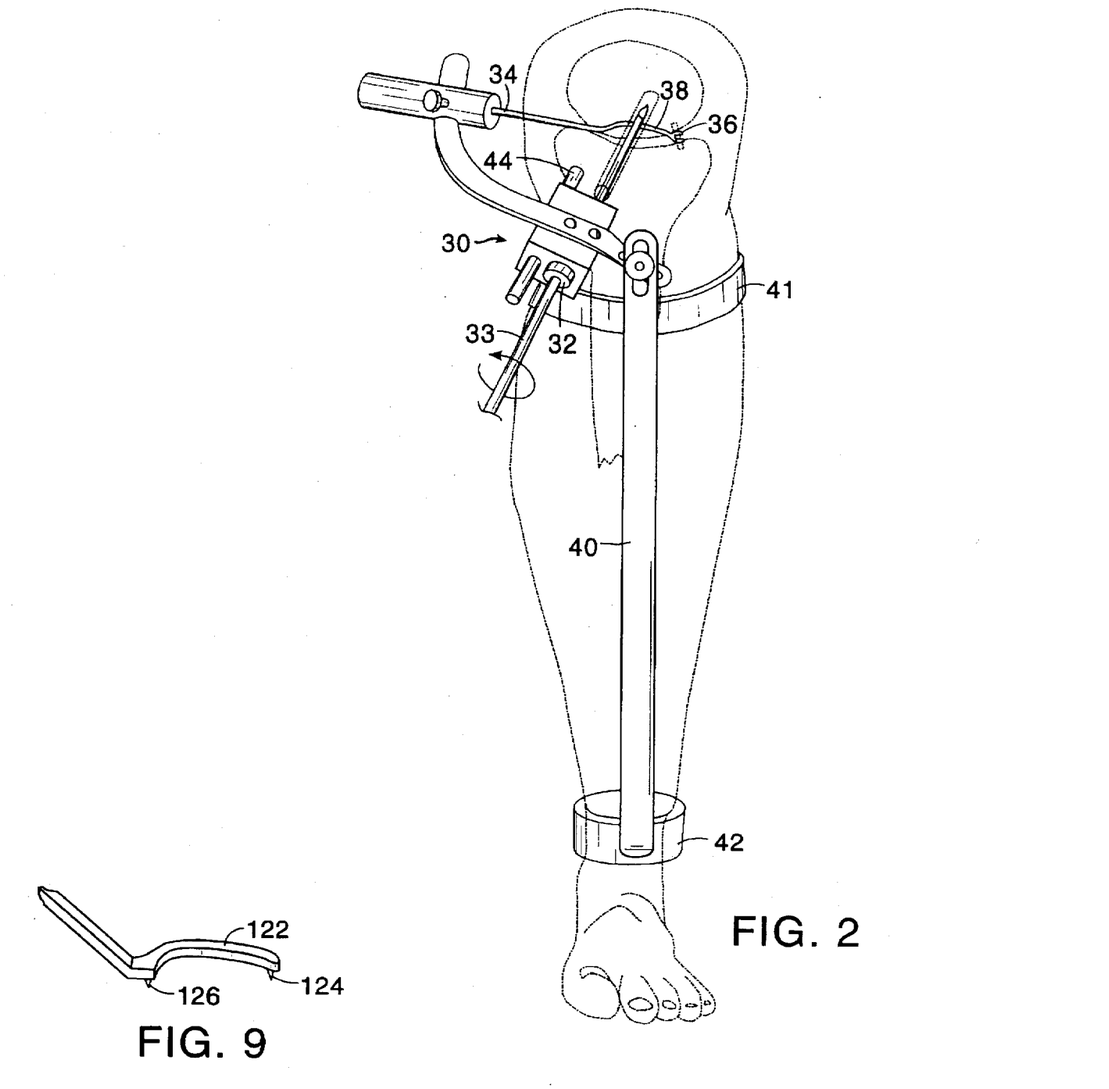
FIG. 2 is an isometric view of a tibial drill guide of the present invention.
FIG. 9 is an isometric view of the distal end of the positioning arm of the tibial guide of FIG. 8.

Referring now to FIG. 2, the tibial guide 30 is shown. A pipe 32 is oriented at approximately 55° to horizontal. The pipe 32 provides a cylindrical tunnel that serves to guide a coring reamer 33 or other drill inserted therethrough. With the patient's leg held fixed at approximately 110° to 120°, the guide can be used for drilling both the tibial tunnel and then the femoral tunnel. Therefore, a portal for the drill is not required behind the femur and a closed tunnel can be drilled. Both tunnels are drilled through the tibia from the anteromedial tibial incision.

A positioning arm 34 is attached to the pipe 32. The positioning arm 34 has a fork 36 at its far end. The fork 36 has two rounded prongs. The fork 36 is attached to an arcuate portion 38 of the arm 34. The arcuate portion 38 allows for maneuverability of the arm 34 within the knee area upon insertion through the anteromedial portal. Meanwhile, the arthroscope is inserted into the knee joint through the distal lateral portal. The fork 36 needs to be placed against the leading edge of the posterior cruciate ligament. The positioning arm 34 is shaped and oriented with respect to the pipe 32 so that the hole drilled by a reamer or drill through the pipe 32 is directed through the tibia to a point approximately 7 millimeters from the leading edge of the posterior cruciate ligament. The center of the tibial tunnel is further defined by the tangent to the center of the inner circumference of the anterior one-third of the lateral meniscus.

An adjustable rod 40 is attached to the pipe 32 at one end. A calf strap 41 secures the guide to the patient's leg. The guide has an ankle strap 42 proximate the opposite end of the rod 40. The rod 40 can be adjusted in length to accommodate different leg sizes. The calf strap 41 and ankle strap 42 provide anchors for achieving and maintaining proper orientation of the pipe 32. The straps are affixed with the fork 36 oriented properly around the PCL attachment on the tibia.

Another anchor to securely orient the pipe 32 is provided by a K-wire 44. The K-wire 44 is shot through the skin of the patient's leg and into the tibia. The K-wire 44 may be positioned on the guide 39 closely adjacent the pipe 32 so that the hole formed in the tibia by the K-wire is adjacent and parallel to the hole to be drilled through the pipe 32. The anchoring provided by the cup 36, the ankle strap 42 and the K-wire 44 stably and correctly position the pipe 32 for guiding a coring reamer or a drill. The tunnels may thus be cored without a guide pin in the core. The tibial tunnel is reamed first and the core removed. The knee is flexed or extended a variable amount in order to properly position the femoral tunnel. A longer coring reamer is then directed through the tibial tunnel for drilling in and through the femur. The bone core from the femur is removed. Standard deburring and debridement procedures are followed.

Figure 8:
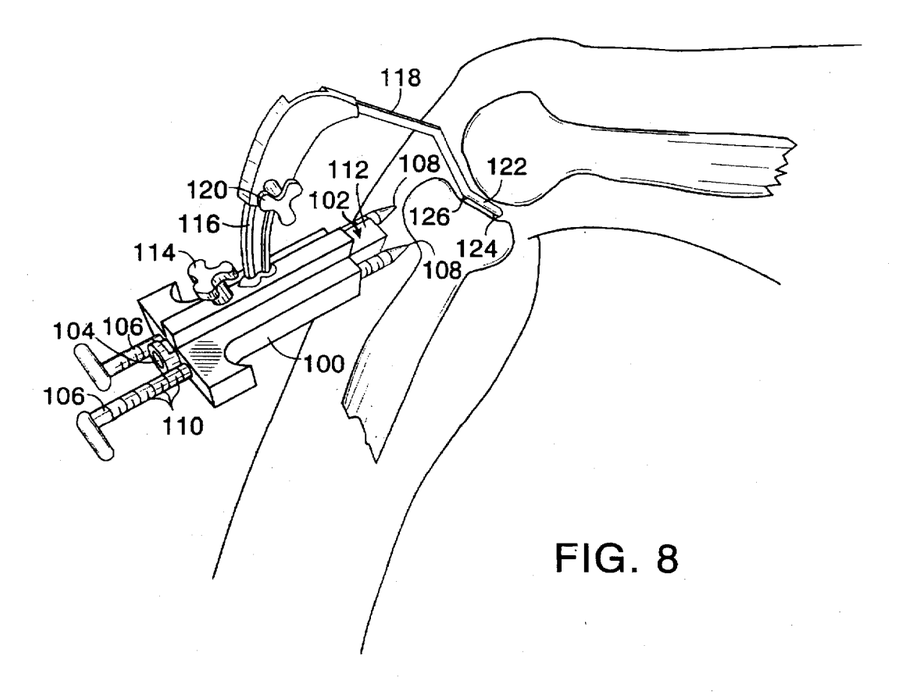
FIG. 8 is an isometric view of a tibial guide of the present invention in use against a knee.

A presently preferred embodiment of the tibial guide is shown in FIG. 8. Rigid stabilization of the guide against the knee is accomplished without the need for an ankle strap. A base 100 has a longitudinal open passage for receiving a guide tube 102. The guide tube 102 has a cylindrical tunnel 104 longitudinally therethrough. Guide tubes may be made with different diameter cylindrical tunnels to accommodate reamers or drills of corresponding diameter. The cylindrical tunnel 104 must be tight enough around the reamer to accurately guide it but wide enough to permit the reamer to rotate therein. On either side of the cylindrical tunnel, anchoring pins 106 or outriggers may be inserted. The two anchoring pins 106 provide two points of stability for the base against the tibia. The anchoring pins 106 have pointed ends 108 that can pierce skin. Therefore, it is not necessary to insert the pins through an incision, and they can be used to poke their own holes. The anchoring pins 106 securely engage the anterior margin of the tibia. The anchoring pins are notched along their length on one side. Inside the base 100, the notches 110 engage internal ridges to act like a ratchet. As the anchoring pins 106 are extended out from the base the notches click against the ridges. The anchoring pins 106 are prevented from retracting by the notches and ridges. To remove an anchoring pin from a patient, the handle on the proximal end of the anchoring pin is turned 180° to disengage the notches from the ridges. Then the anchoring pin can move freely longitudinally in either direction. The handle of the anchoring pin may advantageously be arranged as a flag which points horizontally outward from the base when the notches are engaged and points inward toward the other anchoring pin when the notches are disengaged. The adjustability of the anchoring pins accommodates the variation in leg size encountered from patient to patient.

Once the anchoring pins 106 have been adjusted, the guide tube 102 can also be reciprocally adjusted. The top outer surface 112 of the guide tube preferably has a flat portion for engagement with a set screw. A knob 114 on top of the base can be turned to tighten or release the screw from the guide tube. With the screw released, the guide tube 102 is pushed up against the tibia to thereby provide three points of engagement near the entrance of the tunnel to be drilled.

A curved track 116 is securely attached vertically to the base 100. A positioning arm 118 is adjustably mountable on the curved track. A screw handle 120 on the positioning arm is used to tighten the arm 118 against the vertical track 116. The positioning arm 118 can be slid along the track 116 to assume a range of positions. The range alters the angle made between an axis of the cylindrical tunnel of the guide tube and a seating portion 122 at the distal end of the positioning arm within a range of between about 45°–50° and 80°. By providing a sufficiently large minimum angle of between 45° and 50°, the tibial guide ensures that the tibial tunnel is not drilled at too shallow an angle.

The seating portion 122 of the positioning arm at the distal end of the arm is provided with two anchoring spikes 124 and 126. The spikes project from the end of the positioning arm for insertion into the top of the tibia. The spikes precisely define the exit end of the tunnel to be drilled through the tibia, and thus permit the surgeon to know on inspection and control the tunnel's location. Therefore, it is desirable to place the spikes so that the anatomic center of the anterior cruciate ligament is located midway therebetween. The spikes are sharp so that they may dig into the tibia. A first spike 124 extends from near the end of the positioning arm. The seating portion 122 of the positioning arm is curved between the first spike 124 and a second spike 126. The curve defines and identifies an open region to permit clearance for a coring reamer used in operation to drill a hole through the bone. Thus, the positioning arm does not interfere with the drilling process. Moreover, the seating portion 122 partially encircles the tunnel to be drilled and the spikes are inserted on opposite sides of the tunnel to be drilled. The two spikes on the positioning arm and the two anchoring pins through the base provide four points of stabilization which make for a completely rigid attachment between the tibial guide and the tibia. The attachment is advantageously rigid in three dimensions.

Figure 10:
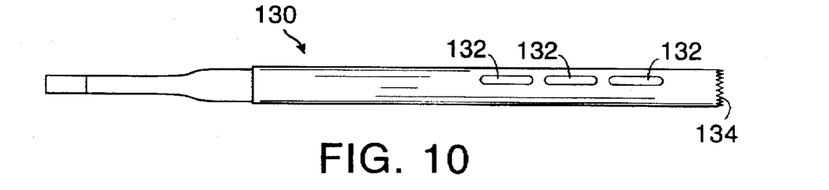
FIG. 10 is an isometric view of a coring reamer of the present invention.

With the tibial guide rigidly attached to the tibia, it is a relatively simple matter to insert the coring reamer through the cylindrical tunnel and drill an accurate tunnel. Advantageously, the bone core is not exposed to the damage ordinarily accompanying the use of a guide wire. However, without the hole through the bone caused by a guide wire, the bone core plugs up the coring reamer with almost fluid-tight engagement. Pulling the bone core out from a conventional coring reamer would be difficult because they are generally solid cylinders. Air or other fluid cannot get in behind the bone core so that pulling on the bore core tends to create a vacuum behind the bone core. The suction of the vacuum pulls the bone core into the coring reamer making it difficult to remove. In accordance with the present invention, a coring reamer 130 is used that is slotted to permit air or fluid in behind the bone core as shown in FIG. 10. The slots or openings 132 are a greater distance from the cutting edge 134 of the reamer than the length of a bone core to be drilled out. A rod can be inserted through a slot or opening behind the bone core to easily push the bone core out from the reamer. A bone core obtained using the tibial guide and coring reamer of the invention may be used and replaced in the body as a part of the graft used for the reconstruction.

Figure 4A:
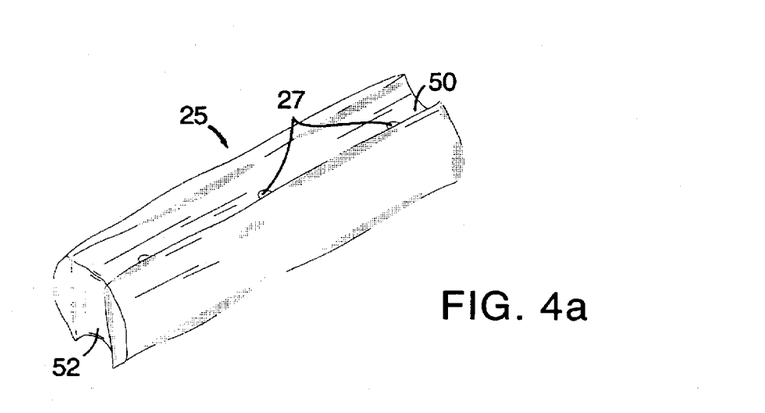
FIG. 4a is an isometric view of a bone plug made by the invention.
Figure 4B:
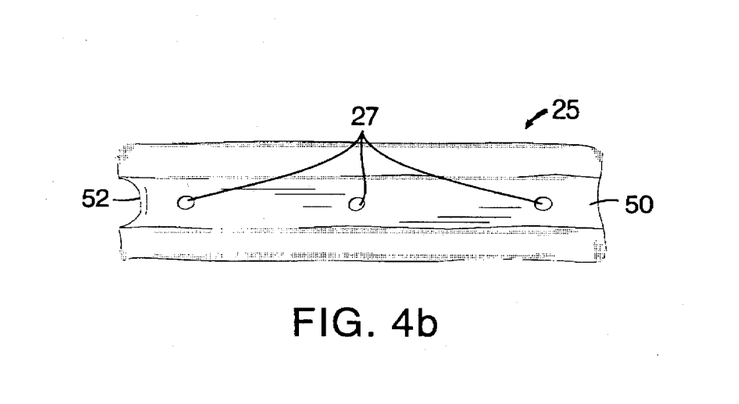

If cores have been drilled out from the bone tunnels they may be used for the bone plugs 25 otherwise, donor bone, namely allograft bone, can be used to make the bone plugs. Referring now to FIGS. 4a and 4b, whatever bone plug 25 is used, two longitudinal substantially parallel grooves 50 are drilled on opposite sides of each bone plug. The grooves provide a recess in which the semitendinosus tendon 20 and gracilis 21 can be seated. A notch 52 may also be drilled, if desired, across one end of the bone plug so that the tendon can be wrapped alongside and around the end of the bone plug, without protruding excessively from the plug. The notch 52 is not required because the bone tunnel is open at each end providing no restriction on the tendon projecting above the end of the graft. It is also advantageous to provide suture holes 27 through the bone plug for attaching the tendon to the plug. The suture holes 27 are drilled into the grooves radially through the bone plug and from one of the substantially parallel grooves 50 to the other. In a presently preferred embodiment, three such suture holes are drilled through the bone plug.

Figure 7A:
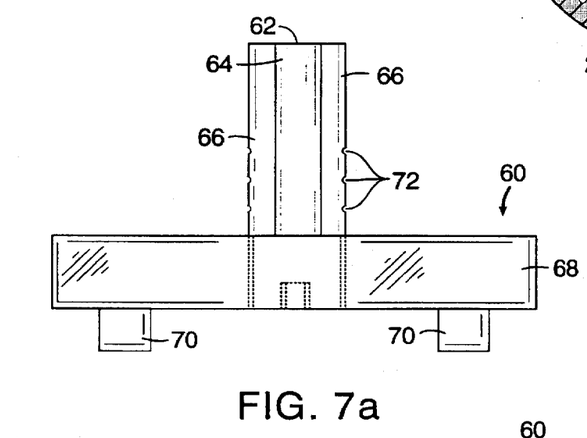
FIG. 7a is a side view of a bone block drill guide.
Figure 7B:
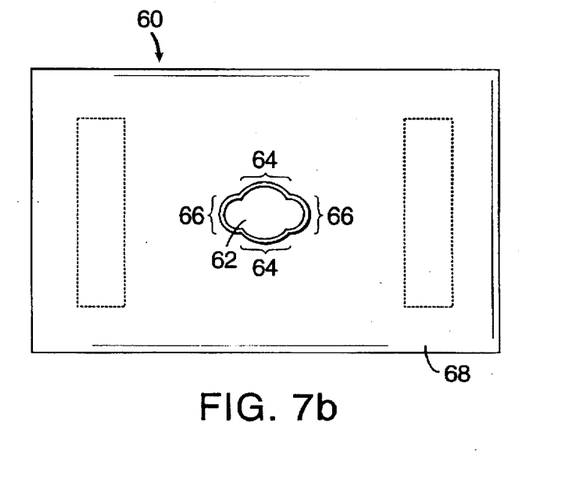

In order to easily and efficiently form a bone core into the desired bone plug for a composite graft, a bone block drill guide 60 of the invention as shown in FIGS. 7a and 7b may be used. The drill guide 60 features a central substantially cylindrical column 62. The central column 62 includes a pair of opposing curved walls 64 having a center of curvature substantially coincident with the center axis through the column 62. The curved walls 64 are shaped so as to hold a bone core parallel with the axis of the column and substantially centered within the column. A second pair of opposing curved walls are arranged at 180° to each other with respect to the central column formed by the curved walls 64. This second pair of walls are the drill guide walls 66. The drill guide walls 66 form two parallel columns on opposite sides of the central column. The drill guide walls 66 have a shorter radius of curvature than the first pair of opposing curved walls 64. In accordance with a presently preferred embodiment, the inner diameter of the drill guide walls 66 is 6 mm whereas the inner diameter of the first pair of opposing walls 64 is 11 mm. The central column 62 is mounted over a base 68. A bone core standing in the central column 62 rests on the base 68. The base 68 is provided with holes therethrough in alignment with the open circular cylinder formed within the drill guide walls 66. The base 68 may also include legs 70 for supporting the drill guide over a table. For drilling suture holes through the bone block, holes 72 are arranged horizontally through the drill guide walls 66. Three holes 72 are preferably aligned in a line.

The substantially parallel grooves 50 are drilled by inserting the bone core or allograft into the center chamber of the column 62 formed by the opposing curved walls 64. A drill is directed in the column 62 along each of the drill guide walls 66 in succession. Thus, parallel grooves 50 are formed on opposite sides of the bone core. The drill may be equipped with a stop to prevent the drill from being directed too far down through the column where it may contact the table beneath. A drill bit inserted through the holes 72 can be easily directed through the center of a groove drilled along the bone core. The suture holes drilled through guide holes 72 preferably extend from one groove to the opposite groove in the bone block.

Figure 5:
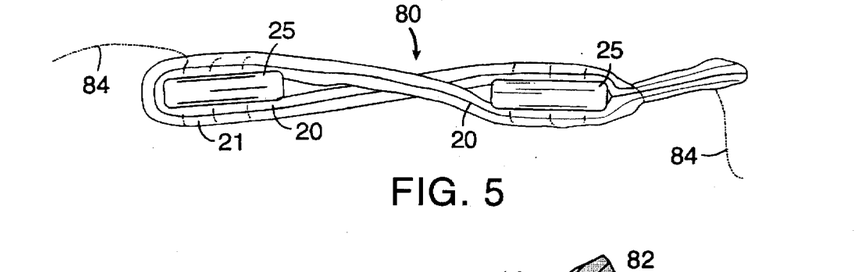
FIG. 5 is a side view of a bone-tendon-bone composite graft made by the present invention.

The semitendinosus tendon 20 and/or gracilis 21 is extended between both of the bone plugs 25. The tendons are seated inside the two substantially parallel grooves 50 and about an end of each bone plug. The tendons are preferably sutured to themselves to form a double loop as shown in FIG. 5. Sutures are also used through the suture holes to attach the tendon to each of the bone plugs. The tendon strands may be straight or twisted between the bone plugs. Twisting will shorten the length of the graft. A ligament replacement of an embodiment of the invention may include both the semitendinosus tendon and the gracilis. As such four strands will connect the two bone plugs. Other embodiments of the invention may use one or the other of the semitendinosus tendon and gracilis. Still further embodiments of the invention may substitute or combine man made or artificial fibers or human tissue for the tendons for use as the ligament replacement.

Figures 3A, 3B:
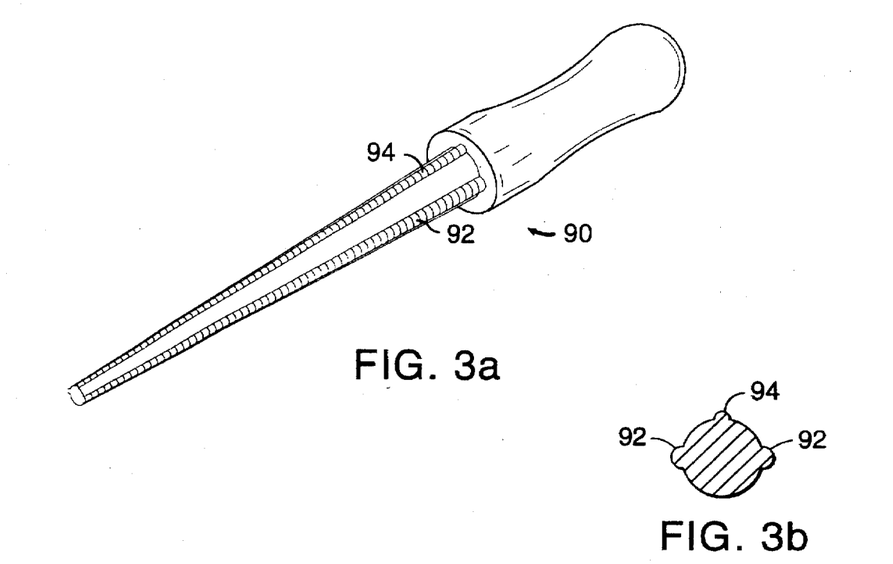

In affixing the composite graft 80 within a bone tunnel, contact between a screw 82 and the tendon should be avoided so as not to cut or tear the tendon. To better insure that the screw is out of contact with the tendon, an interference screw should be driven along the bone portion of the graft between the graft and the bone tunnel wall. A trefoil rasp 90 of the present invention is recommended for use prior to fixation of the graft. As shown in FIGS. 3a and 3b, the trefoil rasp 90 has three longitudinal lobes for use in cutting three channels into each of the bone tunnels. Reciprocating movement of the trefoil rasp 90 in and out of the bone tunnels 16 serves to file away the tunnel walls to form the desired channels. Two of the longitudinal lobes 92 are 180° apart on the rasp. These longitudinal lobes 92 are used to form channels for accommodating the semitendinosus tendons 20 and gracilis 21 seated in the parallel grooves of the bone graft. When the gracilis 21 is attached along and on top of the semitendinosus tendon 20, the channels are required to provide room for the graft to fit within the tunnel.

Figure 6:
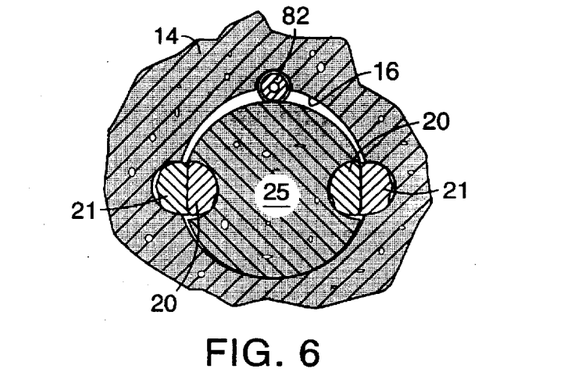
FIG. 6 is a cross-sectional view of FIG. 1 taken along lines 6—6.

The third longitudinal lobe 94 is located parallel to and equidistant from the two opposed lobes. Looking at the end of the rasp as in FIG. 3b, the third lobe 94 is preferably 90° to each of the other two lobes. In the presently preferred embodiment, the third lobe 94 projects 2 mm. from the rasp shaft whereas the other two lobes 92 each project 3 mm. from the shaft. The third lobe 94 advantageously files away a channel along which an interference screw is driven as shown in FIG. 6. The channel helps to maintain the screw straight adjacent the bone portion of the graft. Advantageously, the tibial guide 30 and the trefoil rasp 90 can complement one another in forming the channel for the screw. The hole formed by the K-wire 44 of the tibial guide may be used as the screw channel. To achieve this result, the trefoil rasp should be aligned in the tibial tunnel with its third lobe 94 overlapping into the K-wire hole.

After the channels have been filed in the bone tunnels, the sutures 84 hanging from one end of the composite graft are attached to a needle, a passer or other conventional graft placement tool. The passer is inserted through tibial and femoral bone tunnels and out through the skin on the posterior side of the knee. The passer is removed leaving the suture hanging from the posterior end of the graft and a suture at the other end of the graft hanging out through the tibial incision. The sutures may be pulled on to properly tension and locate the graft within the bone tunnels. Alternatively, the graft may be positioned within the bone tunnels using a pushing device instead of a suture pulling the graft into position.

Fixation of the graft is preferably accomplished with a headless cannulated interference screw. The cannulated interference screw can be carried by a guide wire extending from the tip of an angled driver. The guide wire is preferably a springy wire made of a material such as Nitinol™. The wire extends about 2 centimeters past the end of a screw carried by the driver. For securing the interference screw in the femoral tunnel, the angled or flexible driver and screw are preferably inserted through the anteromedial portal. An angled driver and use thereof is described in co-pending U.S. patent application Ser. No. 07/956,733 filed Oct. 2, 1992, the entire disclosure of which has been incorporated by reference herein. A flexible slide may be used to provide a track to follow from the anteromedial portal to the channel in the femoral tunnel for the interference screw. The insertion of a flexible slide simplifies the guidance of the interference screw into the channel of the femoral tunnel. Once the screw is properly positioned in the tunnel, the driver can initiate screwing and the slide can be removed. The oppositely located channels in the femoral tunnel hold the semitendinosus tendon in position away from the interference screw as it is screwed between the bone portion of the graft and the channel of the bone tunnel. Upon fixation of the interference screw in the femoral tunnel, the angled driver is removed.

The proper tension is then applied to the graft by pulling on the suture hanging out from the tibial incision. A driver and a headless cannulated interference screw are then inserted through the tibial incision for driving the screw along the channel formed in the tibial tunnel. The sutures are cut and the incisions are closed. The reconstructed knee upon fixation of the graft appears as in FIG. 1.

While this operation has been discussed in terms of using autogenous bone cores, alternative sources of bone plugs may be substituted. Allografts, in which donor bone is freeze-dried or fresh frozen for preservation, are one alternative. The freeze drying process kills cells in the bone and may reduce the risk of transmission of infection. Another alternative bone plug is the use of synthetic graft material. With any of these alternatives, the bone plugs may be shaped to appear as described above for the autogenous graft. With the allograft and the synthetic graft, the coring reamer is no longer required and an ordinary drill may be used instead for drilling the bone tunnels.

The surgical technique of the present invention advantageously makes use of the fact that the semitendinosus and gracilis has less morbidity associated with harvesting than does the patellar tendon. It is further advantageous to use a coring reamer and a bone block drill guide of the invention to remove the bone cores from the bone tunnels in the tibia and femur and shape them to accommodate the semitendinosus tendon. The trefoil rasp provides the still further advantage of maintaining alignment of the graft and interference screws in the bone tunnel so that the screw is directed adjacent only the bone portion of the graft.

Of course, it should be understood that various changes and modifications to the preferred embodiments described above will be apparent to those skilled in the art. For example, the bone blocks in the composite graft may be autogenous, allogenic or synthetic. The tendon or other ligament replacement used on the graft may be one or more strands sutured to both of the bone blocks along the grooves. Moreover, alternative equipment may be used for drilling the grooves and the bone plugs. These and other changes can be made without departing from the spirit and the scope of the invention and without diminishing its attendant advantages. It is therefore intended that such changes and modifications be covered by the following claims.

I claim:

1. A method for drilling a tunnel in a bone comprising:
   stably attaching to the bone, a bone-cutting guide having:
      a base including a cylindrical tunnel for guiding a cutting instrument therethrough;
      a positioning arm extending from the base and having a distal end for anchoring the guide against a first region of a bone; and
      an anchoring arrangement attached to the base for contact with a second region of the bone, such that the base is stably oriented with respect to the bone by contact of extensions therewith in at least three locations, counting that of the positioning arm;
   inserting through the cylindrical tunnel of the bone-cutting guide, a coring reamer having a circular cylinder, a cutting edge and openings in the circular cylinder at a distance from the cutting edge greater than the length of a bone core;
   operating the coring reamer through the bone to drill out a bone core; and
   removing the bone core from the coring reamer.

2. A method for drilling a tunnel in a bone comprising:
   anchoring a bone-cutting guide having a cylindrical guide tunnel to at least three locations on the bone;
   inserting a coring reamer through the cylindrical guide tunnel of the bone-cutting guide;
   operating the coring reamer through the bone to drill out a bone core; and
   inserting a pushing member through an opening in the coring reamer to push out the bone core from the coring reamer.

3. A bone-cutting guide comprising:
   a base including a cylindrical tunnel for guiding a cutting instrument therethrough;
   a positioning arm adjustably mounted to the base and having a seating portion at a distal end for seating against a first region of a bone, the seating portion being shaped to define an open region through which the cutting instrument inserted through the cylindrical tunnel can be operated;
   two anchoring pins insertable through the base along opposite sides of the cylindrical tunnel for contacting a second region of the bone; and
   means for ratchet engagement between the base and the two anchoring pins to allow the anchoring pins to be extended from the base but prevent the two anchoring pins from being retracted back into the base.

4. The bone-cutting guide according to claim 3, wherein the bone is the tibia in positions proximate to the knee.

5. The bone-cutting guide of claim 3 wherein the ratchet engagement means of an anchoring pin is disengaged by rotating the anchoring pin about its axis.

6. The bone-cutting guide of claim 3 wherein the cylindrical tunnel is provided within a guide tube that is mounted in the base and is reciprocally adjustable within the base.

7. The bone-cutting guide of claim 3 wherein the positioning arm is adjustably mounted to the base to allow a range of angles between the seating portion and the axis of the cylindrical tunnel.

8. The bone-cutting guide of claim 7 wherein the range of angles is from about 50° to about 80°.

9. The bone-cutting guide of claim 3 to further comprising stabilizing means extending from a distal end portion of the positioning arm for anchoring into the first region of the bone.

10. The bone-cutting guide of claim 9 wherein the stabilizing means comprises a first spike.

11. A tibial guide comprising:
    a base including a cylindrical tunnel for guiding a cutting instrument therethrough;
    two anchoring pins insertable through the base along opposite sides of the cylindrical tunnel;
    a positioning arm adjustably mounted to the base and having a seating portion at a distal end; and
    stabilizing means extending from the seating portion of the positioning arm for anchoring into the tibia within the knee joint.

12. The tibial guide of claim 11 wherein the seating portion is shaped to define an open region through which the cutting instrument inserted through the tunnel can be operated.

13. The tibial guide of claim 11 wherein the stabilizing means comprises a first spike.

14. The tibial guide of claim 13 wherein the stabilizing means further comprises a second spike displaced from the first spike.

15. The tibial guide of claim 14 wherein the seating portion of the positioning arm is curved between the first spike and the second spike so as to define an open region through which the cutting instrument inserted through the cylindrical tunnel is operated.

16. The tibial guide of claim 11 further comprising means for adjusting an angle formed between an axis of the cylindrical tunnel and the seating portion of the positioning arm.

17. The tibial guide of claim 16 wherein the adjusting means can adjust the angle formed between the axis of the cylindrical tunnel and the seating portion between about 50° and about 80°.

18. The tibial guide of claim 16 wherein the adjusting means limits the angle formed between the axis of the cylindrical tunnel and the seating portion to no less than a predetermined angle greater than about 45°.

19. The tibial guide of claim 11 further comprising means for ratchet engagement between the base and the two anchoring pins to allow the two anchoring pins to be extended from the base but prevent the two anchoring pins from being retracted back into the base.

20. The tibial guide of claim 11 wherein the cylindrical tunnel is provided within a guide tube that is mounted in the base and is reciprocally adjustable within the base.

21. A tibial guide comprising:
    a base including a cylindrical tunnel for guiding a cutting instrument therethrough;
    two anchoring pins for attaching the base to the tibia; and
    a positioning arm adjustably mounted to the base and having a seating portion at a distal end for seating against the tibia within a knee joint, the seating portion being shaped to define an open region through which the cutting instrument inserted through the cylindrical tunnel can be operated.

22. The tibial guide of claim 21 further comprising means for adjusting an angle formed between an axis of the cylindrical tunnel and the seating portion of the positioning arm.

23. The tibial guide of claim 22 wherein the adjusting means can adjust the angle formed between the axis of the cylindrical tunnel and the seating portion between about 50° and about 80°.

24. The tibial guide of claim 22 wherein the adjusting means limits the angle formed between the axis of the cylindrical tunnel and the seating portion to no less than a predetermined angle greater than 45°.

25. The tibial guide of claim 21 wherein the two anchoring pins are inserted through the base along opposite sides of the cylindrical tunnel and further comprising means for ratchet engagement between the base and the two anchoring pins to allow the two anchoring pins to be extended from the base but prevent the two anchoring pins from being retracted back into the base.

26. The tibial guide of claim 21 wherein the cylindrical tunnel is provided within a guide tube that is mounted in the base and is reciprocally adjustable within the base.

27. The tibial guide of claim 21 further comprising a first spike and a second spike displaced from one another on the seating portion of the positioning arm for anchoring into the tibia within the knee joint.

28. A bone-cutting guide comprising:

a base including a cylindrical tunnel for guiding a cutting instrument therethrough;

a positioning arm extending from the base and having a distal end for anchoring the guide against a first region of a bone;

two anchoring pins insertable through the base along opposite sides of the cylindrical tunnel for contacting a second region of the bone; and means for ratchet engagement between the base and the two anchoring pins to allow the anchoring pins to be extended from the base but prevent the two anchoring pins from being retracted back into the base.

29. The bone-cutting guide of claim 28 wherein the ratchet engagement means of an anchoring pin is disengaged by rotating the anchoring pin about its axis.

30. The bone-cutting guide of claim 28 further comprising stabilizing means extending from the distal end portion of the positioning arm for anchoring into the first region of the bone.

31. The bone-cutting guide of claim 30 wherein the stabilizing means comprises a first spike.

32. The bone-cutting guide of claim 28 wherein the cylindrical tunnel is provided within a guide tube that is mounted in the base and is reciprocally adjustable within the base.

33. The bone-cutting guide of claim 28 wherein the positioning arm includes a seating portion at the distal end.

34. The bone-cutting guide of claim 33 wherein the seating portion is being shaped to define an open region through which the cutting instrument inserted through the cylindrical tunnel can be operated.

35. A bone-cutting guide comprising:

a base including a cylindrical tunnel for guiding a cutting instrument therethrough;

a positioning arm having a seating portion at a distal end for resting against a first region of a bone, the positioning arm being adjustably mounted to the base to allow a range of angles between the seating portion and the axis of the cylindrical tunnel; and two anchoring pins insertable through the base along opposite sides of the cylindrical tunnel for contacting a second region of the bone, such that the base is stably oriented with respect to the bone by contact of extensions therewith in at least three locations, counting that of the positioning arm.

36. The bone-cutting guide of claim 35 wherein the range of angles is from about 50° to about 80°.

37. The bone-cutting guide of claim 35 wherein the seating portion is being shaped to define an open region through which the cutting instrument inserted through the cylindrical tunnel can be operated.

38. The bone-cutting guide of claim 35 further comprising means for ratchet engagement between the base and the two anchoring pins to allow the anchoring pins to be extended from the base but prevent the two anchoring pins from being retracted back into the base.

39. The bone-cutting guide of claim 38 wherein the ratchet engagement means of an anchoring pin is disengaged by rotating the anchoring pin about its axis.

40. The bone-cutting guide of claim 35 further comprising stabilizing means extending from the seating portion of the positioning arm for anchoring into the first region of the bone.

41. The bone-cutting guide of claim 40 wherein the stabilizing means comprises a first spike.

42. The bone-cutting guide of claim 35 wherein the cylindrical tunnel is provided within a guide tube that is mounted in the base and is reciprocally adjustable within the base.

43. A bone-cutting guide comprising:

a base including a cylindrical tunnel for guiding a cutting instrument therethrough;

a positioning arm having a seating portion at a distal end for seating against a first region of a bone, the positioning arm being adjustably mounted to the base to allow a range of angles between the seating portion and the axis of the cylindrical tunnel, the seating portion being shaped to define an open region through which the cutting instrument inserted through the cylindrical tunnel can be operated; and an anchoring arrangement attached to the base for contact with a second region of the bone, such that the base is stably oriented with respect to the bone by contact of extensions therewith in at least three locations, counting that of the positioning arm.

44. The bone-cutting guide according to claim 43, wherein the anchoring arrangement includes an adjustably extendible anchoring pin insertable into the bone through the base.

45. The bone-cutting guide of claim 43 wherein the range of angles is from about 50° to about 80°.

46. The bone-cutting guide according to claim 43, wherein the anchoring arrangement comprises two anchoring pins insertable through the base along opposite sides of the cylindrical tunnel.

47. The bone-cutting guide of claim 43 further comprising stabilizing means extending from a distal end portion of the positioning arm for anchoring into the first region of the bone.

48. The bone-cutting guide of claim 43 wherein the cylindrical tunnel is provided within a guide tube that is mounted in the base and is reciprocally adjustable within the base.

* * * * *

UNITED STATES PATENT AND TRADEMARK OFFICE
CERTIFICATE OF CORRECTION

PATENT NO. : 5,681,320
DATED : October 28, 1997
INVENTOR(S) : David A. McGuire

It is certified that error appears in the above-identified patent and that said Letters Patent is hereby corrected as shown below:

Column 10, line 7, please delete "to" before "further"

Signed and Sealed this

Twenty-fourth Day of March, 1998

Attest:

BRUCE LEHMAN

*Attesting Officer*        *Commissioner of Patents and Trademarks*